(12) United States Patent
Haras et al.

(10) Patent No.: US 7,798,709 B2
(45) Date of Patent: Sep. 21, 2010

(54) COMPUTED TOMOGRAPHY UNIT AND METHOD FOR A COMPUTED TOMOGRAPHY UNIT HAVING AT LEAST ONE MARKING DEVICE FOR THE POSITIONALLY ACCURATE MARKING OF AN INTERVENTION POSITION BY WAY OF A LASER BEAM ON AN OBJECT TO BE EXAMINED

(75) Inventors: Gabriel Haras, Mücke (DE); Peter Aulbach, Forchheim-Kersbach (DE)

(73) Assignee: Siemens Aktiengesellschaft, Munich DEX ( * ) Notice: Subject to any disclaimer, the term of this patent is extended or adjusted under 35 U.S.C. 154(b) by 220 days.

(21) Appl. No.: 11/476,116

(22) Filed: Jun. 28, 2006

(65) Prior Publication Data

US 2007/0036274 A1 Feb. 15, 2007

(30) Foreign Application Priority Data

Jun. 29, 2005 (DE) .................. 10 2005 030 285

(51) Int. Cl.
*A61B 6/08* (2006.01)
(52) U.S. Cl. .................................... 378/206; 600/426
(58) Field of Classification Search .............. 378/166, 378/206; 600/426
See application file for complete search history.

(56) References Cited

U.S. PATENT DOCUMENTS

| 5,873,826 | A * | 2/1999 | Gono et al. ............ 600/425 |
| 6,041,249 | A * | 3/2000 | Regn .................... 600/429 |
| 6,044,291 | A * | 3/2000 | Rockseisen ............. 600/429 |
| 6,048,097 | A * | 4/2000 | Heinze .................. 378/206 |
| 6,269,143 | B1 * | 7/2001 | Tachibana ............... 378/65 |
| 6,829,500 | B2 * | 12/2004 | Landi et al. ............. 600/426 |
| 2002/0099284 | A1 * | 7/2002 | Herrmann ............... 600/407 |
| 2004/0145886 | A1 * | 7/2004 | Fatemi et al. ............ 362/35 |
| 2005/0119559 | A1 * | 6/2005 | Van Vaals et al. ........ 600/425 |
| 2009/0234370 | A1 * | 9/2009 | Haras .................... 606/130 |

FOREIGN PATENT DOCUMENTS

DE 100 57 027 6/2002

* cited by examiner

*Primary Examiner*—Hoon Song
*Assistant Examiner*—Mona M Sanei
(74) *Attorney, Agent, or Firm*—Harness, Dickey & Pierce, P.L.C.

(57) ABSTRACT

A computed tomography unit and a method are disclosed, for a computed tomography unit having at least one marking device for the positionally accurate marking of an intervention position by way of a laser beam on an object to be examined. The at least one marking device is assigned to a rotary frame of the computed tomography unit and is arranged directly in a recording plane of a recording system. As such, a positionally accurate marking of an intervention position with the aid of simple devices/methods is possible without a large numerical outlay, particularly even during operation of the computed tomography unit, that is say during a rotational movement of the rotary frame.

18 Claims, 5 Drawing Sheets

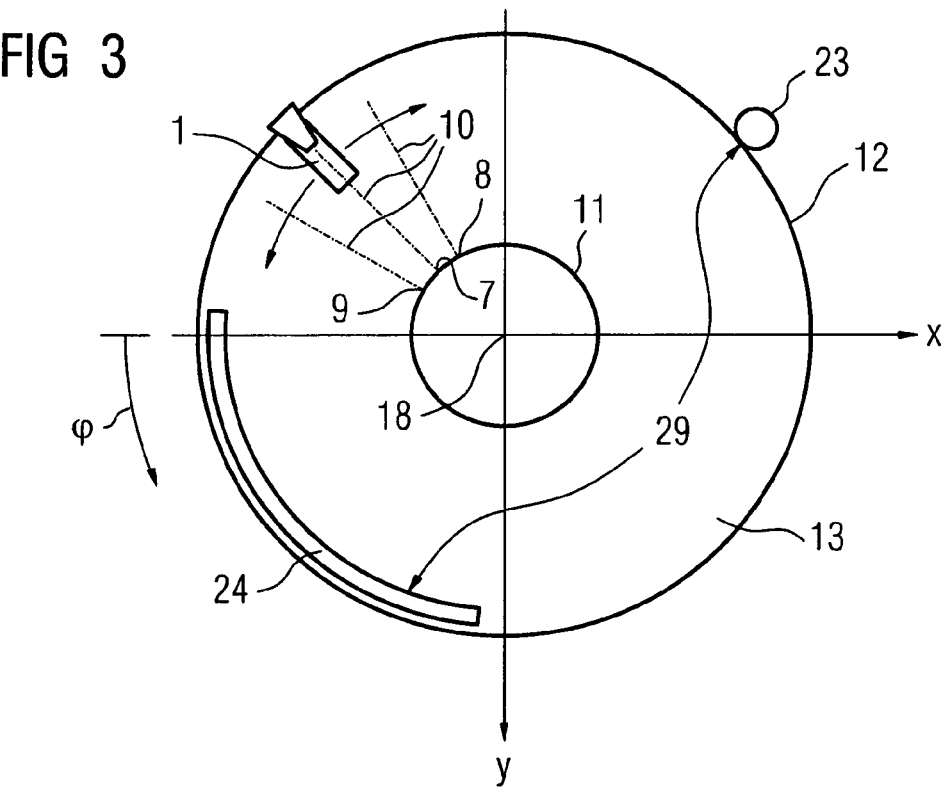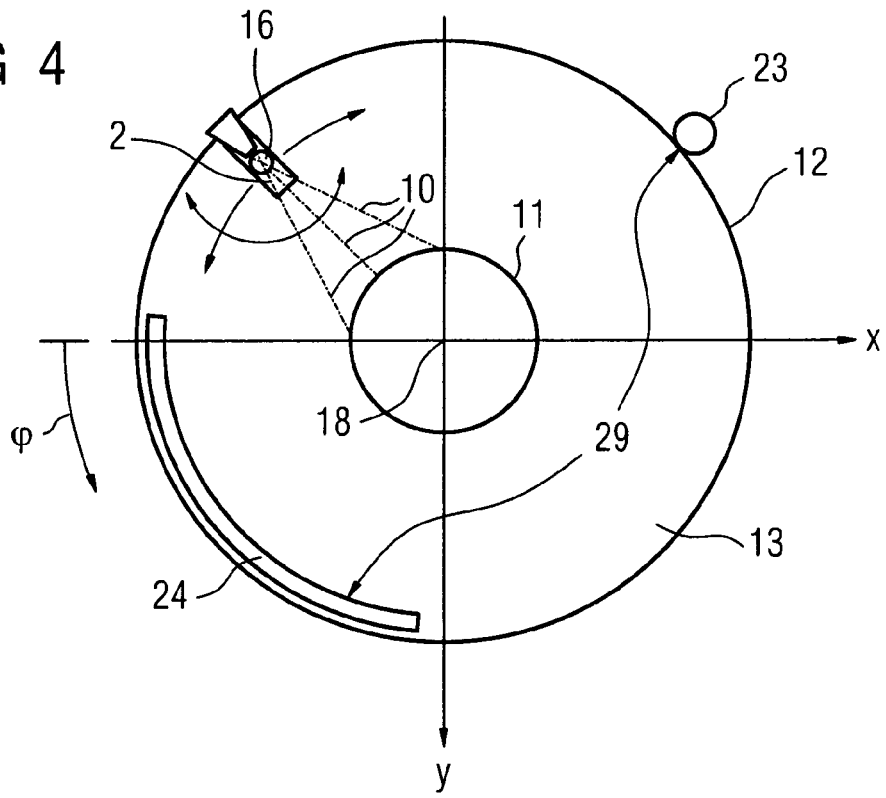

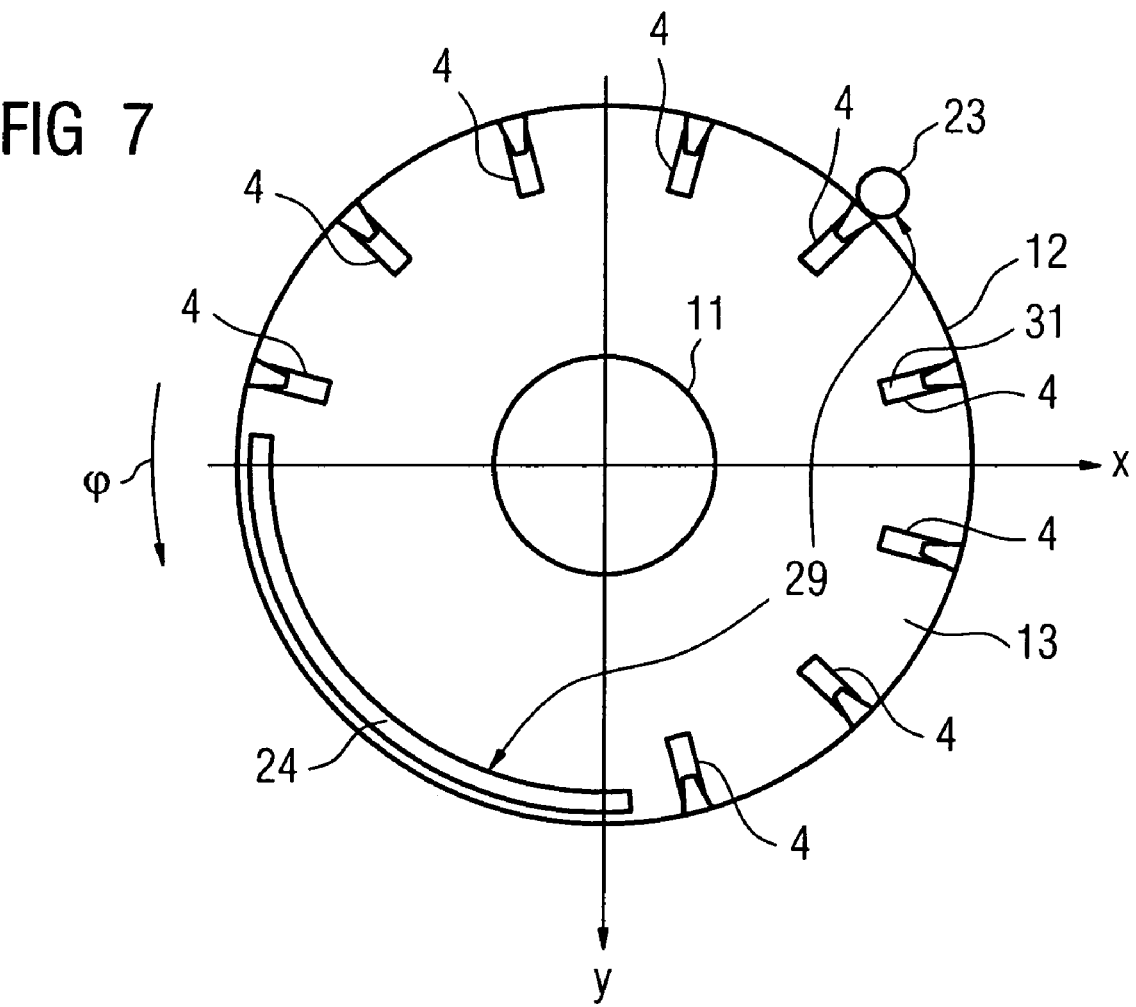

COMPUTED TOMOGRAPHY UNIT AND METHOD FOR A COMPUTED TOMOGRAPHY UNIT HAVING AT LEAST ONE MARKING DEVICE FOR THE POSITIONALLY ACCURATE MARKING OF AN INTERVENTION POSITION BY WAY OF A LASER BEAM ON AN OBJECT TO BE EXAMINED

PRIORITY STATEMENT

The present application hereby claims priority under 35 U.S.C. §119 on German patent application number DE 10 2005 030 285.8 filed Jun. 29, 2005, the entire contents of which is hereby incorporated herein by reference.

FIELD

The invention generally relates to a computed tomography unit and/or a method for a computed tomography unit. For example, it may generally relate to one having a marking device for the positionally accurate marking of an intervention position by way of a laser beam on an object to be examined.

BACKGROUND

During a surgical procedure, it is advantageous in advance of the intervention to fix and to mark the accurate intervention position as a function of the anatomy of a patient and as a function of the type of operation so that no organs situated in the treatment area are damaged by the operation.

DE 100 57 027 A1 discloses for this purpose a marking method with the aid of which a penetration point and/or penetration angle at an examination object can be identified by a laser beam of a laser light sight. The laser light sight is assigned in this case to a C arm of an x-ray device, and can be adjusted in the plane defined by the C arm. In advance of the treatment, a planning scan of the area to be treated is carried out in order to identify the penetration point. Subsequently, there is marked in the volume image produced during the planning scan an intervention position on the basis of which the laser light sight is adjusted such that the intervention position marked in the volume image corresponds as well as possible to the position identified by the laser beam of the laser light sight.

The calculation of the adjusting positions of the laser light sight that are required for this purpose is possible only with a substantial numerical outlay and given accurate knowledge of the position of the laser light sight with reference to the recording system or with reference to the volume image produced.

SUMMARY

At least one embodiment of the invention includes a computed tomography unit and/or a method for a computed tomography unit with the aid of which a positionally accurate marking of an intervention position is possible with the aid of simple devices/methods.

The inventors, in at least one embodiment, have realized that a marking of an intervention position with the aid of a marking device in the case of a computed tomography unit is possible with high precision with the aid of simple devices/methods precisely when the marking device is assigned to the rotary frame of the computed tomography unit, and is arranged directly in the recording plane of the recording system. This arrangement renders it possible for the positions of the marking device and the positions, identified by an operator, for a surgical procedure to be respectively specified in the same coordinate system in an image that has been produced during a planning scan. Thus, the transformations between the different coordinate systems of the image produced and of the marking device, which are complicated to carry out, are dropped from in the calculation of the adjusting positions of the marking device that are required for marking the intervention position on the object.

According to at least one embodiment of the invention, the computed tomography unit thus includes at least one marking device for the positionally accurate marking of an intervention position by way of a laser beam on an object to be examined, and a rotary frame for holding a recording system arranged in a recording plane, the at least one marking device being assigned to the rotary frame and being arranged directly in the recording plane of the recording system.

In addition to the intervention position, the laser beam can likewise simultaneously emit in a direction of an intervention to be carried out for the purpose of angularly accurate marking of an intervention angle. This offers the advantage that a longitudinally extended intervention instrument cannot only be placed with positional accuracy in a way that is precise for the operation, but can subsequently also be aligned in three dimensions with reference to the object or the patient. The three dimensional alignment is performed intuitively by bringing the longitudinal axis of the intervention instrument into the path of the laser beam. As soon as the instrument is located in the beam path, the end of the instrument is illuminated by the laser beam such that a simple optical feedback is made available to the operator for the purpose of monitoring correct alignment of the instrument.

In an advantageous variant of at least one embodiment of the invention, the marking device(s) can be adjusted about a first adjusting axis that is aligned perpendicular to the recording plane, so that the laser beam produced by the marking device(s) can be adjusted in the recording plane in a very flexible way.

One advantageous refinement of at least one embodiment of provides in addition that the marking device(s) can be adjusted about a second adjusting axis that lies in the recording plane and is aligned perpendicular to an imaginary connecting line between the marking device(s) and a center of rotation of the rotary frame. By arranging an adjusting axis in a tangential alignment with the periphery of the rotary frame, it is therefore advantageously possible also to display intervention positions that are located outside the recording plane.

The marking device(s) preferably include a plurality of laser diodes that are arranged around the periphery of the rotary frame in the direction of rotation of the rotary frame. An intervention position and/or an intervention angle can even be used in this case without rotationally adjusting the rotary frame merely by activating that laser diode which is located at the determined adjusting position.

A particular advantage of such marking device(s) resides in the possibility that the intervention position or the intervention angle can even be displayed during operation of the computed tomography unit, that is to say during a rotational movement of the rotary frame. To this end, the marking device(s) can advantageously be driven by way of a control apparatus in such a way that the laser beam can be activated synchronously with the rotational movement for the purpose of irradiating in a stationary fashion. In the simplest case, this is achieved with the aid of a plurality of laser diodes by virtue of the fact that, as a function of the rotation angle position assumed by the rotary frame, the laser diodes are activated temporarily at the angle positions defined by the intervention position and/or by the intervention angle.

The method of at least one embodiment, for the positionally accurate marking of an intervention position by way of a laser beam on an object to be examined, usually comprises:

a) acquiring projections of at least one subregion of the object, b) reconstructing an image of the subregion, c) marking a position in the image, d) adjusting the marking device in order to identify the intervention position on the object on the basis of the marked position, the marked intervention position on the object corresponding at least substantially to the identified position in the image.

BRIEF DESCRIPTION OF THE DRAWINGS

An example embodiment of the invention and further advantageous refinements of the invention are illustrated in the following schematics, in which:

FIG. 3 shows a frontal view of a rotary frame of the computed tomography unit with a first variant of a marking device, FIG. 4 shows a frontal view of the rotary frame from FIG. 3 with a second variant of a marking device that has a first adjusting axis that is aligned perpendicular to the recording plane, FIG. 7 shows a frontal view of the rotary frame with a fourth variant, fastened thereon, of a marking device, the marking device being formed from a plurality of laser diodes.

DETAILED DESCRIPTION OF THE EXAMPLE EMBODIMENTS

Figure 1:
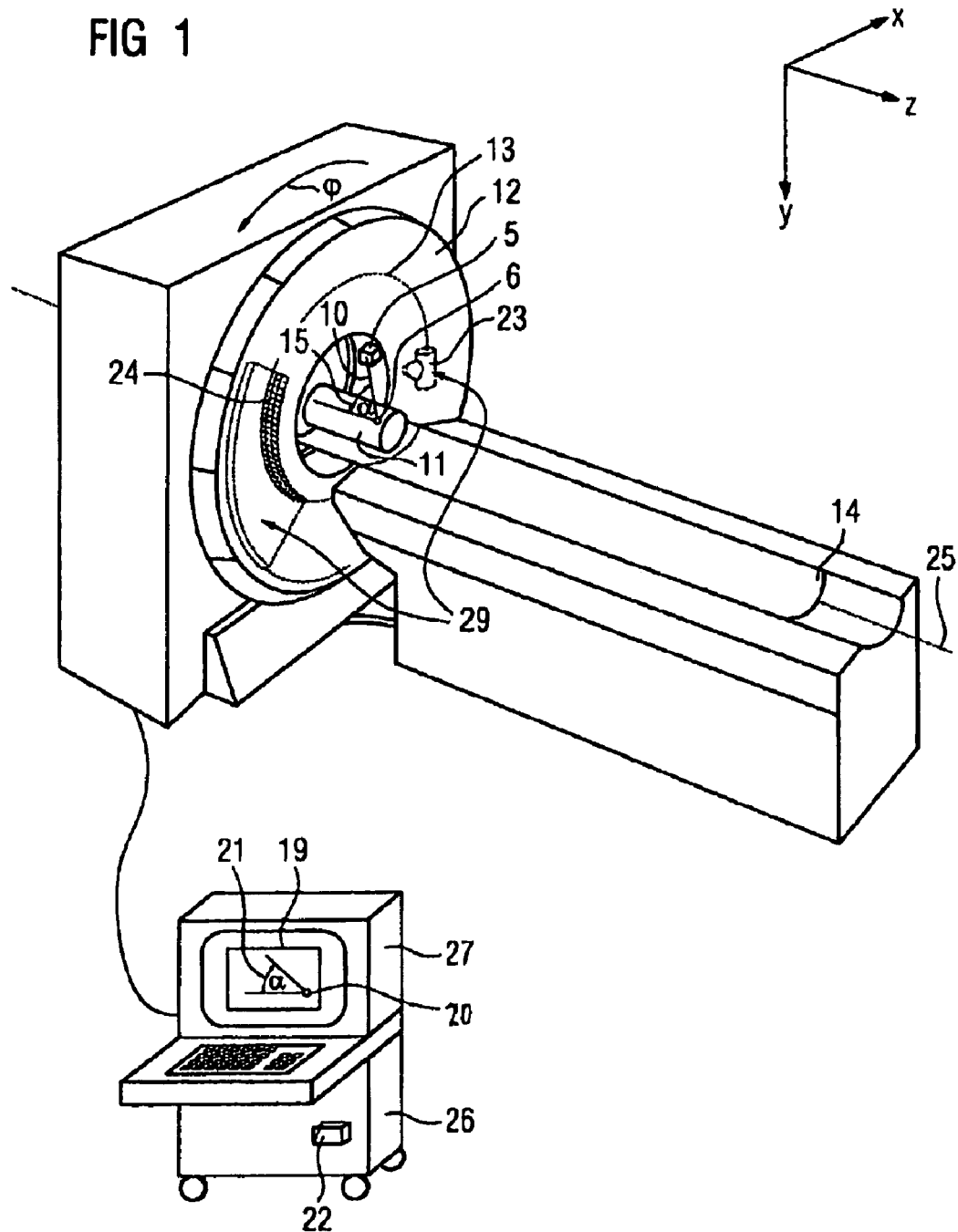
FIG. 1 shows a computed tomography unit according to an embodiment of the invention having a marking device for the positionally accurate marking of an intervention position and/or an intervention angle, in a perspective illustration.

FIG. 1 illustrates the computed tomography unit according to at least one embodiment of the invention for the positionally accurate marking of an intervention position 6 and/or of an intervention angle 15 by way of a laser beam 10 on an object 11 to be examined, in a perspective view. The computed tomography unit includes a recording system 29 arranged in a recording plane 13. The recording plane 13 is aligned parallel to a plane that is defined by the x- and y-axes of a rectangular coordinate system illustrated in FIG. 1. An x-ray source 23, here in the form of an x-ray tube, and a detector 24 are part of the recording system and are fitted on a rotary frame 12 in a fashion situated opposite one another such that during operation of the computed tomography unit an x-ray beam emanating from a focus of the x-ray source 23 and delimited by marginal rays impinges on the detector 24.

The rotary frame 12 can be set rotating about a rotation axis 25 in the φ-direction shown, this being done by way of a drive device that is not illustrated. The rotation axis 25 runs parallel in this case to the z-axis of the coordinate system. Projections from different projection directions can in this way be acquired in the recording plane 13 for an object 11, for example for a patient, located on a measuring table 14; the projections are subsequently converted into an image 19 by calculation, for example into a volume image.

The computed tomography unit further has a marking device 5, for example in the form of a laser diode, that is suitable for marking the intervention position 6 and/or the intervention angle 15. The marking device 5 is arranged directly in the recording plane 13 on the rotary frame 12 of the computed tomography unit. The position thereof can be specified on the basis of this arrangement in a coordinate system in which pixels of an image 19 produced by scanning the object 11 are also described. Complicated conversions between different coordinate systems when determining an adjusting position of the marking device 5 for irradiating the intervention position 6 and/or the intervention angle 15 are therefore not required on the basis of an identified position 20 and/or an angle 21 in the image 19 produced.

The computed tomography unit further has a computing device 26 for converting the projections acquired by the recording system 29 into the image 19 by calculation. Moreover, it is also possible to use the computing device 26 to execute computer programs with the aid of which the position 20 and/or the angle 21 of the intervention can be identified in the image 19 illustrated on a display unit 27. Furthermore, the computing device 26 is used for the purpose of determining the adjusting position of the marking device 5 from which the intervention position 6 and/or the intervention angle 15 are/is irradiated. Moreover, the computing device is set up such that the marking device 5 can be adjusted to the adjusting position determined.

Figure 2:
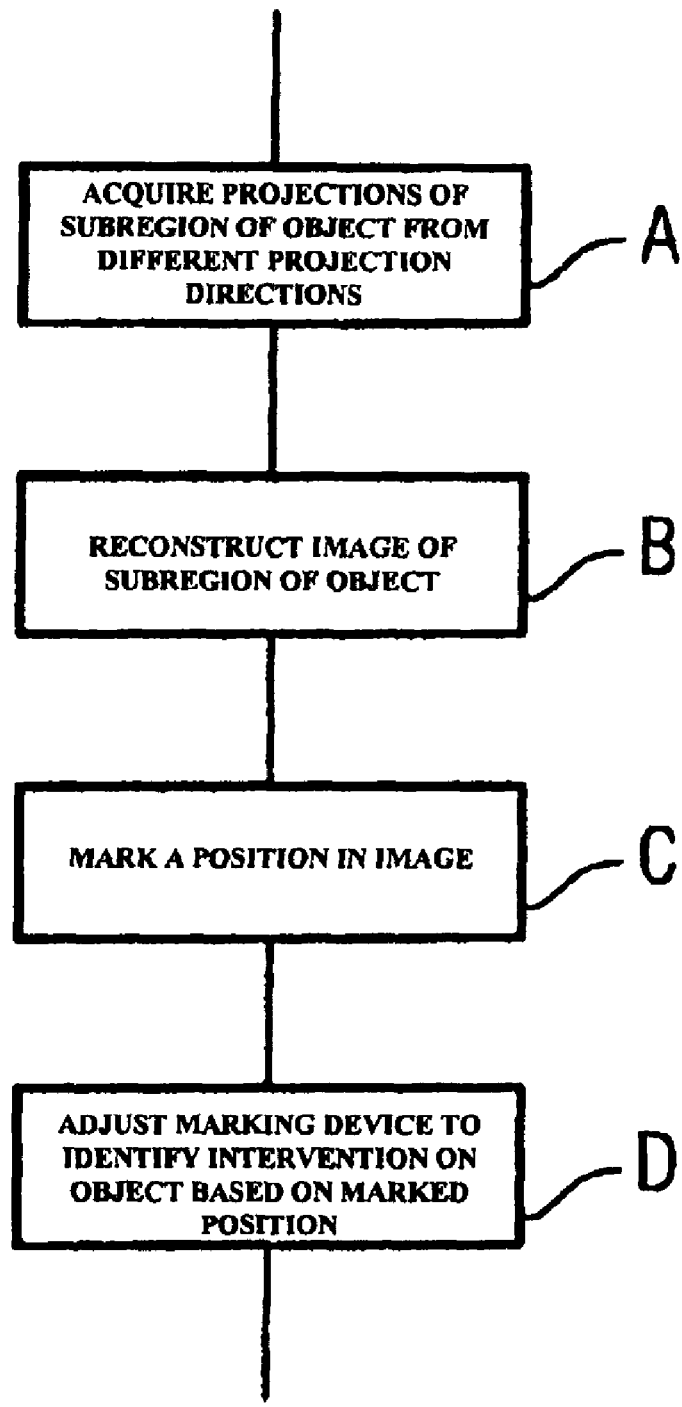
FIG. 2 shows a method according to an embodiment of the invention for a computed tomography unit for marking an intervention position, in the form of a block diagram.

A method according to at least one embodiment of the invention for the positionally accurate marking of the intervention position 6 and/or the intervention angle 15 by way of the laser beam 10 on the object 11 to be examined typically includes the following illustrated in FIG. 2:

In a first method step A, projections from different projection directions are required from at least one subregion of the object 11. Subsequently, the projections acquired by a data acquisition unit that is not represented are transferred to the computing unit 16 and reconstructed there in a method step B to form the image 19 of the subregion. Subsequent thereto, the image 19 is displayed on the display unit 27 such that it is possible by way of an input unit 28, for example a keyboard or a mouse, to mark in a method step C that position 20 in the image 19 which is intended for the intervention. In addition to the position 20, however, the intervention angle 15 can also be identified in the form, for example, of a vector with the aid of the input unit 28. The adjusting position of the marking device 1 from which the intervention position 6 and/or the intervention angle 15 can be irradiated is calculated below on the basis of the position 20 and/or the angle 21 identified in the image 19.

The adjustment of the marking device 5 for marking the intervention position 6 on the object 11 and/or the intervention angle 15 is performed in a final method step D. Depending on the intervention, it can be necessary in some circumstances for the purpose of marking not only to adjust the marking device 5, but also to adjust the position of the measuring table 14 or the position of the object 11 in the direction of the x-axis.

It is conceivable that the marking of the intervention position 6 and/or the intervention angle 15 is performed during operation, that is to say during a rotational movement of the rotary frame 12. To this end, the computed tomography unit has a control apparatus 22 with the aid of which the marking device 5 is driven such that the laser beam 10 can be activated synchronously with the rotational movement for the purpose of irradiating at least the intervention position 6 in a stationary fashion. The laser beam 10 of the marking device 5 is thus activated only once for a fraction of a second per revolution of the rotary frame 12. In the case of modern computed tomography units of recent generation, high revolution rates are achieved, and so the intervention position 6 is irradiated several times per second.

FIG. 3 shows a frontal view of the rotary frame 12 of the computed tomography unit with a first variant of a marking device 1. The marking device 1 emits in the direction of a center of rotation 18 of a rotational movement executed by the rotary frame 12. Different intervention positions 7,8,9 can be irradiated by virtue of the fact that the marking device 1 is adjusted into different rotary angle positions by a rotation of the rotary frame 12. FIG. 4 shows a second variant of a marking device 2 in the case of which the marking device 2 can additionally be adjusted about a first adjusting axis 16 that runs perpendicular to the recording plane 13. Given this additional degree of freedom of the adjustment, the marking device 2 can irradiate all the intervention angles of a surgical procedure carried out in the recording plane 13.

Figure 5:
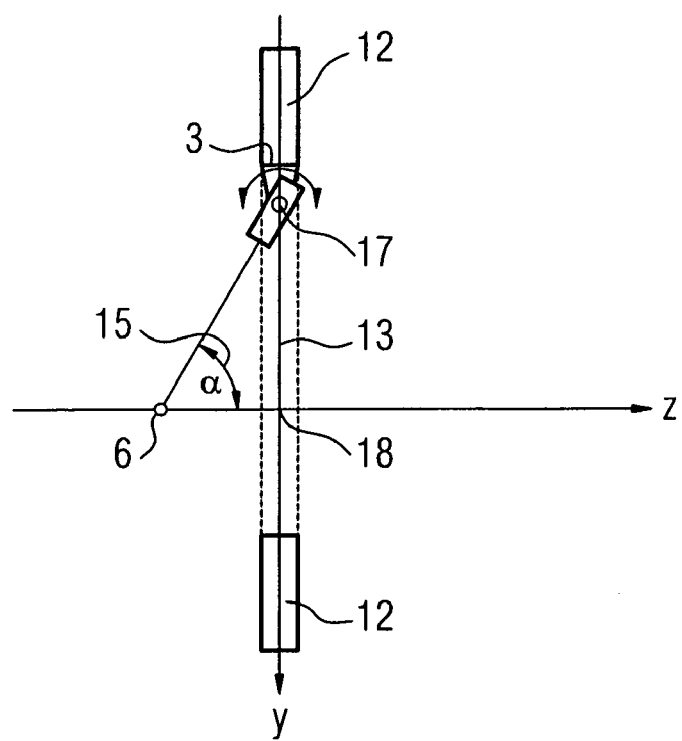
FIG. 5 shows a side view of the rotary frame from FIG. 3 with a third variant of a marking device that has a second adjusting axis that lies in the recording plane and is aligned perpendicular to an imaginary connecting line between the marking device and a center of rotation of the rotary frame.
Figure 6:
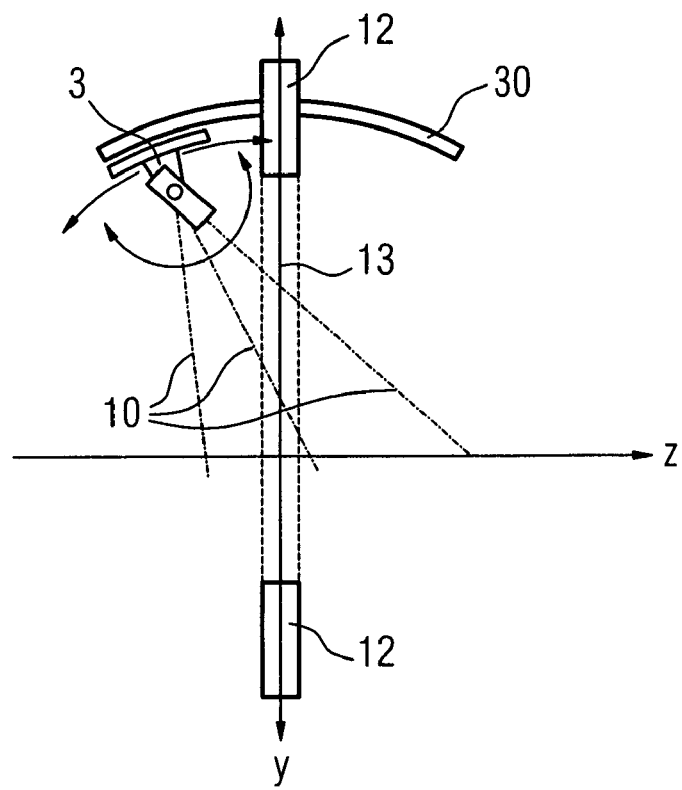
FIG. 6 shows the marking device from FIG. 5, the marking device being supported on a rail for the purpose of adjustment in the direction of the z-axis.

FIG. 5 shows the rotary frame 12 illustrated in FIG. 3 in a side view with a third variant of a marking device 3 that has a second adjusting axis 17 which lies in the recording plane 13 and is aligned perpendicular to an imaginary connecting line between the marking device 3 and the center of rotation 18 of the rotary frame 12. The third variant of the marking device 3 is particularly suitable for irradiating intervention positions that are located outside the recording plane 13. A particularly high degree of flexibility with reference to the marking of an intervention position 6 and/or an intervention angle 15 with the aid of the marking device 3 obtains, as shown in FIG. 6, when the marking device 3 is additionally supported on a rail 30 such that the marking device 3 can also assume different positions in the direction of the z-axis.

FIG. 7 shows a frontal view of the rotary frame 12 with a fourth variant of a marking device 4 in the case of which the marking device 4 is formed from a plurality of laser diodes 31, only one being provided with a reference numeral, and the laser diodes 31 being arranged around a periphery of the rotary frame 12 in the direction of rotation f of the rotary frame 12. Intervention positions and/or intervention angles can result in this case even without rotary adjustment of the rotary frame 12, simply by activating a single laser diode 31 that is located at the adjusting position determined.

It is possible, furthermore, for the intervention position and/or the intervention angle to be displayed in a simple way even during operation of the computed tomography unit, that is to say during a rotational movement of the rotary frame 12. To this end, the laser diodes 31 can be activated with the aid of the control apparatus 22 in a synchronous fashion with the rotational movement for the purpose of irradiating the intervention position and/or the intervention angle in a stationary fashion. By contrast with a single laser, the corresponding intervention position or the intervention angle is irradiated not only once per revolution, but n times, n being the number of the laser diodes 31.

The marking device(s) used in these example embodiments in the form of a laser or of laser diodes are of a purely example nature. It would likewise be conceivable to form the marking device(s) as a mirror or a system composed of mirrors, which mirror or system is assigned to the rotating part of the gantry and is irradiated by a laser in a way appropriate for marking the intervention position and/or the intervention angle. It is immaterial here whether the laser is arranged in the recording plane of the computed tomography unit or on the rotating part of the gantry. The only requirement for marking is that each mirror can be adjusted by way of a control unit in such a way that the laser beam emanating from the laser effects a marking of the intervention position and/or the intervention angle.

The nature of at least one embodiment of the invention can be summarized as follows: at least one embodiment of the invention relates to a computed tomography unit and/or a method for a computed tomography unit having at least one marking device 1;2;3;4;5 for the positionally accurate marking of an intervention position 6;7;8;9 by way of a laser beam 10 on an object 11 to be examined, the at least one marking device 1;2;3;4;5 being assigned to a rotary frame 12 of the computed tomography unit and being arranged directly in a recording plane 13 of a recording system 29 such that a positionally accurate marking of the intervention position 6;7;8;9 is possible with simple devices/methods without a large numerical outlay, in particular even during the operation of the computed tomography unit, that is to say during a rotational movement of the rotary frame 12.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computed tomography unit, comprising:
   at least one marking device configured to positionally accurately mark an intervention position by way of a laser beam on an object to be examined; and
   a closed rotary frame, the closed rotary frame being configured to hold a recording system arranged in a recording plane, the marking device being attached to the closed rotary frame and being arranged directly in the recording plane of the recording system, wherein
   the closed rotary frame is configured to rotate completely around the object, the recording system and the at least one marking device are configured to rotate, along with the closed rotary frame, completely around the object within the recording plane, and the at least one marking device is configured to be driveable by way of a control apparatus in such a way that the laser beam is activateable synchronously with a rotational movement of the closed rotary frame to irradiate at least the intervention position in a stationary fashion during the rotational movement, the at least one marking device being configured to irradiate the intervention position by activating once for each rotation of the closed rotary frame.

2. The computed tomography unit as claimed in claim 1, wherein the laser beam, for marking an intervention angle with angular accuracy, radiates onto the intervention position in a direction of an intervention to be carried out.

3. The computed tomography unit as claimed in claim 2, wherein the at least one marking device is adjustable about a first adjusting axis that is aligned perpendicular to the recording plane.

4. The computed tomography unit as claimed in 2, wherein the marking device is adjustable about a second adjusting axis that lies in the recording plane and is aligned perpendicular to an imaginary connecting line between the marking device and a center of rotation of the rotary frame.

5. The computed tomography unit as claimed in claim 1, wherein the at least one marking device is adjustable about a first adjusting axis that is aligned perpendicular to the recording plane.

6. The computed tomography unit as claimed in 5, wherein the marking device is adjustable about a second adjusting axis that lies in the recording plane and is aligned perpendicular to an imaginary connecting line between the marking device and a center of rotation of the rotary frame.

7. The computed tomography unit as claimed in claim 1, wherein the at least one marking device is adjustable about a second adjusting axis that lies in the recording plane and is aligned perpendicular to an imaginary connecting line between the marking device and a center of rotation of the rotary frame.

8. The computed tomography unit as claimed in claim 1, wherein the at least one marking device includes a plurality of laser diodes that are arranged around a periphery of the rotary frame in a direction of rotation of the rotary frame.

9. A method for a computed tomography unit including at least one marking device to positionally accurately mark an intervention position by way of a laser beam on an object to be examined, the computed tomography unit further including a closed rotary frame holding a recording system arranged in a recording plane, the at least one marking device being attached to the closed rotary frame and arranged directly in the recording plane of the recording system, the method comprising:
    acquiring projections of at least one subregion of the object;
    reconstructing an image of the subregion;
    marking a position in the image;
    adjusting the at least one marking device to identify the intervention position on the object on the basis of the marked position, the intervention position on the object corresponding at least substantially to the identified position in the image, the closed rotary frame rotating completely around the object, the recording system and the at least one marking device rotating completely around the object, along with the closed rotary frame, within the recording plane, wherein
    during a rotational movement of the closed rotary frame, the at least one marking device is driveable by way of a control apparatus in such a way that the laser beam is activated synchronously with the rotational movement to irradiate at least the intervention position in a stationary fashion, and the at least one marking device irradiates the intervention position by activating once for each rotation of the closed rotary frame.

10. The method as claimed in claim 9, wherein, in addition to the position, an angle is also marked in the image, and the at least one marking device for identifying an intervention angle on the basis of the marked angle is adjusted such that the intervention angle corresponds at least substantially to the identified angle in the image.

11. The method as claimed in claim 10, wherein the at least one marking device is adjusted about a first adjusting axis that is aligned perpendicular to the recording plane.

12. The method as claimed in claim 10, wherein the at least one marking device is adjusted about a second adjusting axis that lies in the recording plane and is aligned perpendicular to an imaginary connecting line between the at least one marking device and a center of rotation of the rotary frame.

13. The method as claimed in claim 9, wherein the at least one marking device is adjusted about a first adjusting axis that is aligned perpendicular to the recording plane.

14. The method as claimed in claim 13, wherein the at least one marking device is adjusted about a second adjusting axis that lies in the recording plane and is aligned perpendicular to an imaginary connecting line between the at least one marking device and a center of rotation of the rotary frame.

15. The method as claimed in claim 9, wherein the at least one marking device is adjusted about a second adjusting axis that lies in the recording plane and is aligned perpendicular to an imaginary connecting line between the at least one marking device and a center of rotation of the rotary frame.

16. The method as claimed in claim 9, wherein the at least one marking device includes a plurality of laser diodes that are arranged around a periphery of the rotary frame in a direction of rotation of the rotary frame, and in which the laser beam is produced by at least one of the laser diodes.

17. A computed tomography unit, comprising:
    a marking means for positionally accurate marking of an intervention position by way of a laser beam on an object to be examined; and
    a closed rotary frame configured to hold a recording system arranged in a recording plane, the marking means being assigned attached to the closed rotary frame and being arranged directly in the recording plane of the recording system, wherein
    the closed rotary frame is configured to rotate completely around the object, the recording system and the marking means are configured to rotate, along with the closed rotary frame, completely around the object within the recording plane, and the marking means is driveable by way of a control apparatus in such a way that the laser beam is activateable synchronously with a rotational movement of the closed rotary frame for the purpose of irradiating at least the intervention position in a stationary fashion during the rotational movement, the marking means being configured to irradiate the intervention position by activating once for each rotation of the closed rotary frame.

18. The computed tomography unit as claimed in claim 17, wherein the marking means includes a plurality of laser diodes that are arranged around a periphery of the rotary frame in a direction of rotation of the rotary frame.

* * * * *